(12) United States Patent
Forsell et al.

(10) Patent No.: US 9,888,999 B2
(45) Date of Patent: Feb. 13, 2018

(54) ACELLULAR DERMAL ALLOGRAFTS AND METHOD OF PREPARATION

(75) Inventors: James Forsell, San Rafael, CA (US); Frank Fan, San Rafael, CA (US)

(73) Assignee: Aziyo Biologics, Inc., Richmond, CA (US)

( * ) Notice: Subject to any disclaimer, the term of this patent is extended or adjusted under 35 U.S.C. 154(b) by 1283 days.

(21) Appl. No.: 13/389,937

(22) PCT Filed: Jan. 4, 2010

(86) PCT No.: PCT/US2010/000003
§ 371 (c)(1),
(2), (4) Date: Sep. 27, 2012

(87) PCT Pub. No.: WO2011/019361
PCT Pub. Date: Feb. 17, 2011

(65) Prior Publication Data
US 2013/0013068 A1    Jan. 10, 2013

Related U.S. Application Data

(60) Provisional application No. 61/233,098, filed on Aug. 11, 2009.

(51) Int. Cl.
*A61F 2/10* (2006.01)
*A01N 1/02* (2006.01)

(52) U.S. Cl.
CPC ............ *A61F 2/105* (2013.01); *A01N 1/0294* (2013.01)

(58) Field of Classification Search
CPC ............................... A61F 2/105; A01N 1/0294
See application file for complete search history.

(56) References Cited

U.S. PATENT DOCUMENTS

| | | | |
|---|---|---|---|
| 5,336,616 A | 8/1994 | Livesey et al. | |
| 5,613,892 A | 3/1997 | Goldstein | |
| 5,613,982 A | 3/1997 | Goldstein | |
| 2003/0185702 A1* | 10/2003 | Burgess | A01N 1/02 422/22 |
| 2004/0219133 A1* | 11/2004 | Lyles | 424/93.7 |
| 2005/0221484 A1 | 10/2005 | Boyce | |
| 2006/0073592 A1* | 4/2006 | Sun | A01N 1/00 435/423 |
| 2006/0275377 A1* | 12/2006 | Gomes | A01N 1/02 424/569 |
| 2007/0269791 A1 | 11/2007 | Takami et al. | |
| 2010/0047308 A1* | 2/2010 | Kim | A61L 27/3683 424/423 |

(Continued)

OTHER PUBLICATIONS

International Search Report of PCT/US2010/000003 dated Aug. 31, 2010.

(Continued)

*Primary Examiner* — Louise W Humphrey
*Assistant Examiner* — Stephen A Perkins
(74) *Attorney, Agent, or Firm* — Winston & Strawn LLP

(57) ABSTRACT

A method for preparing a sterilized human acellular dermal allograft where the dermal allograft is sterilized by irradiation and has a greatly reduced bio-burden and enzymatic and antigenic activity. This product line of allografts can be easily used by surgeons in soft tissue replacement or repair and has an extended shelf life, of up to at least about three years.

21 Claims, 1 Drawing Sheet

(56) References Cited

U.S. PATENT DOCUMENTS

2010/0185219 A1* 7/2010 Gertzman ............ A61L 31/005
606/151

OTHER PUBLICATIONS

Supplementary European Search Report of EP 10 80 8431 dated Jul. 3, 2012.
Sok-Siam Gouk et al., "Alterations of human acellular tissue matrix by gamma irridation: Histology, biomedical property, stability, in vitro cell repopulation, an remodeling". J. of Biomedical Mat. Research Part B Applied Biomaterials. vol. 84B, Issue 1, May 11, 2007, 205-217.
C.D. Richters et al., "Development of a dermal matrix from glycerol preserved allogenic skin". Cell Tissue Banking, 2008, 9:309-315.
Anthony P. Sclafani et al., "Evaluation of Acelluar Dermal Grafta (AlloDerm) sheet for Soft Tissue Augmentation". Arch Facial Plastic Surg. Apr.-Jun. 2001, vol. 3, pp. 101-103.

* cited by examiner

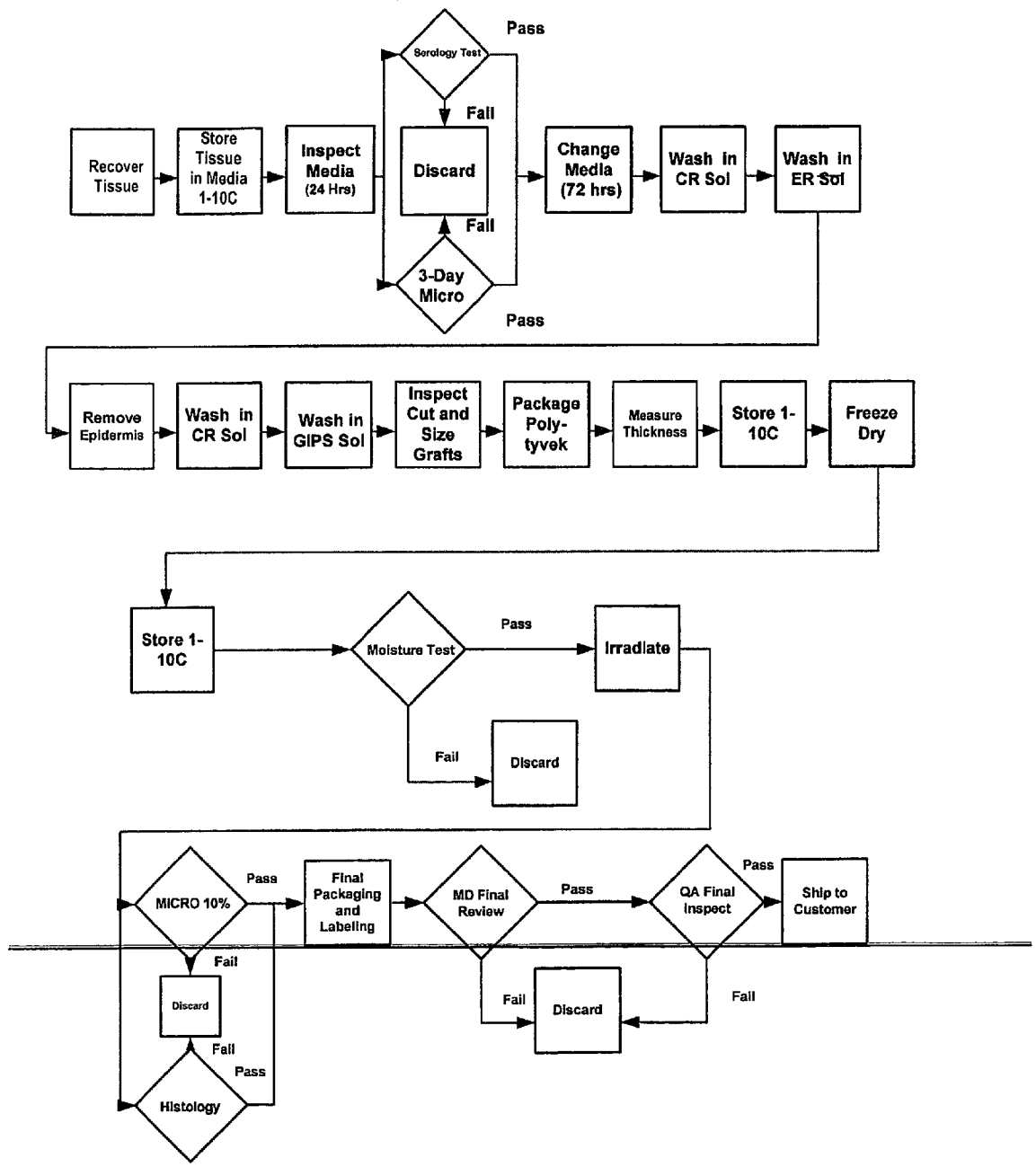

ACELLULAR DERMAL ALLOGRAFTS AND METHOD OF PREPARATION

This application claims priority from U.S. Provisional Application No. 61/233,098, filed Aug. 11, 2009.

BACKGROUND OF THE INVENTION

Field of the Invention

The present invention generally relates to the field of tissue processing and grafting; particularly to a method for preparing sterilized human acellular dermal ("ACD") allografts that may be stored for prolonged periods before use.

Background of the Prior Art

Skin has the same overall structure in all vertebrate organisms. It is made of an exterior layer called the epidermis, a basement membrane layer, a dermis layer, and a subcutaneous layer of adipose tissue and protein fibers. Of course, skin tissue removed from any vertebrate cadaver may contain additional attached soft tissue.

The epidermis is a thin, elastic, waterproof outer layer of the skin. It contains a majority of the cells found in the skin. The majority of the cells in the epidermis are keratinocytes. The tough, fibrous-like protein produced by these cells is known as keratin. Keratinocytes are self-replacing cells; the keratinocytes in the lower (interior) portion of the epidermis divide and push upward over time to replace older keratinocytes, which eventually reach the skin's outer surface and are sloughed off. Also, present in the epidermis is the pigment producing melanocyte. Another cell type, the Merkel cell, is also present in the epidermis. It is easiest to think of this cell as a receptor, which is in contact with nerve endings grown into the dermis layer. Yet another cell type in the epidermis is the Cells of Langerhan, part of the immune system, which are produced in the bone marrow. In-situ all these cells can migrate through and repopulate a skin graft, whether or not it includes epidermis.

The basement membrane is a thin but complex layer. Its molecular structure is of such a nature as to provide a mechanism to hold the skin together. When preparing allografts, artisans skilled in the art deem it is critical to provide dermal skin with an essentially intact basement membrane. See U.S. Pat. No. 5,336,616.

The dermis is comprised primarily of collagen, which gives the skin structure and strength. Dermis also contains elastin, which is responsible for the skin's flexibility. The collagen and elastin are produced by fibroblast cells residing in the dermis. The upper part of the dermis contains a papillary layer, having molecules that help bind the dermis to the epidermis. Blood vessels grow into the dermis, spreading into the upper part of the dermis.

The skin is a critical organ. Deep injuries to the skin, if not treated promptly, can lead to loss of life. The skin provides protection against foreign infectious agents, prevents fluid loss, and helps regulate body temperature. Treatment of injuries to the skin, in particular deep injuries, often requires the use of skin allografts. When skin allografts are used in burn or other topical (skin replacing skin) applications, immune cells from the patient, fibroblast cell precursors, and other cell types press against the epidermis and slough off the allograft, as healing occurs. Often, it is preferred that an autograft is provided, if such skin tissue, in sufficient quantity and quality, is available by surgical removal from another part of the same person's body or can be timely generated (grown/expanded-cultured) from a patient's own skin. This approach (the use of skin obtained surgically from the same patient) would render moot the issue of immune rejection of the allograft. Often, however, skin from a cadaver, or even skin from some animals (xenograft) is used instead of an autograft.

Fresh skin allografts have many limitations. One limitation is their short storage life, making their availability an issue. Typically, complications can result from issues of immunogenicity and sterility with these allografts. However, out of necessity, such allografts are used because the temporary benefit of covering the wound while the patients repair and defenses build up outweighs any complications arising from sterility and of the eventual immune rejection of the allografted skin.

Tissue banks have minimized the disease transmission risk of skin allografts with careful donor screening (medical history) practices, serological testing, microbiological testing, applying certain antibiotics, and with the utilization of sterile technique throughout the tissue handling, processing, storage, and distribution stages. During recovery of either split thickness skin (epidermis and dermal tissue), the area of skin recovery is extensively scrubbed, shaved, and disinfected. The entire surgical process is aseptic and the recovered allograft is stored in media containing antibiotic(s). Although practices may vary between tissue banks, the prevailing tissue recovery methods and standards are in accordance with the American Association of Tissue Banks (AATB) Standards. The AATB Standards reflect best practices in every aspect of tissue bank work and include bank organization, collection, transport, processing and distribution of tissue. See Standards for Tissue Banking, 12th edition, Implementation Date Jun. 1, 2008, co-edited by K. Pearson, N. Dock, and S. Brubaker, Library of Congress Card No. 84-7269.

However, bacteria and fungal infections, as well as viral disease transmission cannot be entirely eliminated. Most products have limited shelf life. Skin allografts comprising epidermis are well suited for skin replacement applications but are not well suited for procedures including periodontal procedures, hernia repair, or wrapping around metal plates and pins. The dermal portion of the skin, which is the topic of the present invention, is better suited to these applications. Dermal allografts retaining cellular content are also not well suited for some procedures, and increase likelihood of immune rejection and infection. A sterile, pliable acellular dermal allograft, which is easy to use in surgical settings, has reduced immunogenicity, can be more easily repopulated by the patient's own cells and can be stored safely for a longer time, would be advantageous. Ideally, the product would be a terminally sterilized acellular dermal allograft, which would eliminate the potential for infection from the donated skin to the recipient. A terminally sterilized acellular product is easier for doctors to use because it is sterilized and conforms to standard operating room procedures.

SUMMARY OF THE INVENTION

In one aspect, the invention provides a method of preparing an irradiation sterilized acellular dermal allograft that can be stored for periods of at least about 3 years before use in grafting procedures. The method comprises obtaining skin tissue; processing the skin by serial exposure, first to a first cell removal solution, followed by exposure to an epidermis removal solution; removing the epidermis to produce a dermal allograft; optionally again exposing the allograft to a cell removal solution; exposing the allograft to a gamma (γ) irradiation protection solution; placing the allograft in a storage container; preparing the allograft for irradiation by performing at least one step from among: drying the allograft by freeze drying (lyophilization), freezing the allograft or placing the allograft in saline; and exposing the allograft to irradiation; whereby the skin tissue can then be stored until use for periods of up to at least about 3 years. Optionally, before the processing step, the skin may be stored in glycerol at −20° C. to 10° C. for up to about 5 years. Prior to storage in glycerol, the graft is treated by exposure to at least two increasing concentration of glycerol, the lowest concentration being about 25% (v:v) and the highest about 100% (v:v). Preferably, the exposure to increasing concentration of glycerol, comprises exposure to 50%, 75% and 100% glycerol (v:v).

In accordance to one embodiment, the cell removal solution comprises at least two detergents. One of the at least two detergents is deoxycholate at a concentration of about between 1% to 10% (v:v).

In accordance to another embodiment, the epidermis removal solution comprises about between 0.2% and 2% (v:v) detergent.

In accordance to yet another embodiment, the γ irradiation protection solution comprises at least two sugars and one sugar is trehalose.

In accordance to still another embodiment, the container is a bag made of polyethylene and spunbond high density polyethylene fiber (Poly-Tyvek®).

In accordance to still yet another embodiment, the skin tissue is placed in a stabilization media prior to exposure to a first cell removal solution. In a further embodiment, the stabilization media is a cell growth media which contains an antibiotic. In accordance to yet still another embodiment, the step of preparing the allograft for irradiation comprises placing the allograft in saline inside a container and in which case, the step of exposure to the γ irradiation protection solution is optional.

In accordance to a further still embodiment, after the step of preparing the allograft for irradiation, the allograft may be stored for up to about one year before irradiation.

In yet still further embodiment, the radiation is γ-radiation. In another embodiment, the γ-radiation is from $Cobalt^{60}$ or $Cesium^{137}$. Preferably, the irradiation is from $Cobalt^{60}$.

In accordance to one aspect of the invention, the irradiation delivers an absorbed radiation dose of 5-35 kGy. Preferably, the absorbed radiation dose is about 10-23 kGy, and, more preferably, the absorbed radiation dose is about 17-23 kGy.

In one aspect, the invention provides a sterile acellular dermal allograft whose characteristics comprise:

the allograft was made sterile by having absorbed between about 5-35 kGy γ-irradiation;

the allograft has an intact matrix and is pliable;

the allograft has a reduced cellular content, reduced bioburden and reduced immunogenicity properties;

the allograft has ductility, re-cellularization, adhesion and revascularization properties significantly similar to a non-irradiated dermal allograft; and the allograft has a shelf life of up to at least about 3 years. The dermal allograft may be used in soft tissue repair.

In accordance to one embodiment, the dermal acellular allograft has absorbed 10-23 kGy of irradiation, preferably 17-23 kGy of irradiation.

In accordance to another embodiment, irradiation is from $Cobalt^{60}$ or $Cesium^{137}$.

BRIEF DESCRIPTION OF THE DRAWINGS

FIG. 1 is a flow chart illustrating primary processing steps for a terminally sterilized, full thickness, freeze-dried acellular dermal allograft, according to one embodiment of the present invention.

DETAILED DESCRIPTION OF THE INVENTION

The current invention provides a method for preparing an acellular dermal (ACD) allograft and the allograft produced thereby, where the allograft is sterile or has a greatly reduced bio-burden, contains no viable cells, and has a long shelf life, i.e. can be easily used by surgeons in soft tissue replacement or repair for a period of time of up to at least about 3 years. The ACD remains pliable. The process of preparation includes exposure of the allograft to radiation, preferably γ-radiation, more preferably $Cobalt^{60}$ or $Cesium^{137}$ radiation, although other sources and types of energy such as x-ray and electron beam may be used. The preferred timing of the irradiation step is towards the end of the overall process, after removal of cells and the epidermis from the allograft and after its packaging, i.e. the allograft preferably is "terminally sterilized." The terminally sterilized allograft in its package remains sterile until opened and exposed to the environment at the time of the surgical procedure. This minimizes the chance of the allograft becoming contaminated before used in a patient. However, sterilization by irradiation might occur earlier in the process of preparing the dermal allograft.

The terminally sterilized allograft of the invention is prepared from human skin and, more preferably, it is from a recently deceased human (cadaver), for use in allografting. However, this invention can be applied also to autografting and xenografting.

FIG. 1 illustrates a flow chart of the steps of the method of the present invention, according to one embodiment. The order of the steps listed in FIG. 1 is illustrative of only one embodiment of the invention. Some of the steps listed in FIG. 1 are optional, as discussed herein elsewhere. FIG. 1 relates, in particular, to incorporation of a freeze drying alternative step and the preparation of full thickness dermal allograft.

The method of recovery/removal of the skin from the cadaver, the requirements for a medically acceptable skin-tissue source, and the transport for use in transplantation are, in many respects, similar to the methods and the standards of the industry. The methods and typical standards are in accordance with the American Association of Tissue Banks' Current STANDARDS FOR TISSUE BANKING, supra. The method of recovering and qualifying tissue includes recovery from, preferably, a recently deceased cadaver (i.e. within 24 hrs of asystole if the cadaver was kept in cooling conditions, but within about 15 hrs, if the cadaver was kept at room temperature), obtaining extensive information about the donor, to include the medical condition, a medical and social history, tissue donor consent, serology reports, physical assessment by the skin surgical recovery team, hemodilution assessment, and an autopsy report.

The skin obtained for the invention is recovered from any suitably sized area of the body, but preferably, it is from the back or the posterior and anterior parts of the legs. It can be recovered using a dermatome or by using other surgical instruments. The dermatome process and equipment is similar in most ways with the standardized use of this medical instrument by burn surgeons. The dermatome is likelier to produce an initial graft having a more even thickness and comprising less adipose tissue. "Extra-Thick" (sometimes referred to as "Xtra thick") is recovered by well-established surgical procedures using standard surgical instruments other than dermatome. The thickness of Xtra thick will range from about 1.50 mm to about 3.00 mm, sometimes up to about 4.0 mm. Full thickness is recoverable by dermatome or possibly surgical instruments. The range of thickness for an original full-thickness graft is from about 0.20 mm to about 2.00 mm. For an allograft destined for use in breast reconstruction or abdominal repair—which requires a thicker and stronger tissue, often the method of choice is Extra-Thick. These terms are well understood by artisans of ordinary skill in the art. An artisan skilled in the art will know which method to use to obtain, Extra-Thick, full thickness or dermatome prepared tissue, and which tissue is more appropriate, depending on the source of the skin and its intended use.

After recovery, the skin, in accordance to the invention is typically placed in a storage/transport media (also referred to as "stabilization" media). A number of media are suitable, such as various cell culture media, often including at least one antibiotic. A preferred media is Roswell Park Memorial Institute 1640 (RPMI 1640), including gentamycin as an antibiotic. RPMI 1640 is a well-known cell culture and tissue storage/transport media. Its composition is known. Artisans skilled in the art often use the RPMI media supplemented with components, such as antibiotic(s) or growth factors, or essential amino acids, or other common supplements for a variety of purposes. RPMI 1640 is available commercially from, inter alia, Sigma-Aldrich Corporation, St. Louis, Mo. The media composition was initially published by Moore et al., JAMA 199:8, pgs. 519-524 (1967).

Samples of the media after exposure to the recovered tissue (typically after about 24 hrs. of exposure) undergoes microbiology testing to determine presence of contaminants. Preliminary results are available within about three days, final results take up to about 12 days. Currently, required serology tests on the donor of the dermis/skin include HIV, hepatitis, T-lymphotropic virus and syphilis. The test results are reviewed before final processing of the tissue and unsuitable tissue is discarded at whatever processing step it has reached when the test results are reviewed.

It is required by the AATB to change the media at least every 72 hours until processing starts. The skin should not be kept in the media (even with periodical changes of the media) for more than 14 days after retrieval. The recovered skin in media is kept at a temperature of between 1° C. to 10° C. (see Standard for Tissue Banking 12th Edition, American Association of Tissue Banks. Section E4.110 Refrigerated Tissue). If the skin is shipped to a different facility (a processing facility), the temperature range required for the duration of the transportation are the same as for storage.

At the processing facility (which can be the same facility as the initial tissue recovery facility), the skin is processed to obtain the desired thickness, to remove adipose and other soft tissue, and to trim away uneven edges and any defective areas. The desired thicknesses of the processed skin allograft ranges from about 0.2 to about 4.0 mm. The desired thickness is determined by consideration of the surgeon's needs and intended use. The thickness range might change over time as required by the standard of practice in the surgical applications.

After the skin has been recovered and trimmed, but prior to further processing, the skin is, optionally, subjected to glycerol treatment to remove water from the skin. The process requires treatment with increasing concentrations of glycerol, starting with a concentration of at least about 25%, ending with exposure to up to about 100% glycerol, each at a temperature of from about 10° C. to about 10° C., preferably at about 4° C. At each of at least two such concentrations, the skin is placed in at least about 1 to 4 volumes of the glycerol solution (to one volume of skin), for from about 1 hour to about 24 hours. If possible, the solution is agitated during at least a portion of this time. The agitation is at between approximately 50 rpm and 200 rpm. Preferably, the skin is exposed to three glycerol concentrations, about 50%, 70%, and 100% glycerol, each for about 1-24 hours. The skin product can be then stored in 100% glycerol at a temperature of from about −20° C. to about 10° C., for up to about five years.

The above glycerol protocol is optional for the performance of the present invention. Typically, it is used when the fresh skin is not processed before the 14 days expiration date for fresh skin tissue.

Prior to processing to remove the epidermis and cells, the glycerol is removed by washing the skin with a normal saline solution or equivalent. Preferably, there are at least two washes, each of about 1 to 5 volumes of saline solution or equivalent to the volume of the skin, with agitation at 50¬1200 rpm, each wash for between 15 and 120 minutes. Of course, if the above glycerol processing step is skipped, the saline wash step may be skipped as well.

The process to remove cells and the epidermis includes separate washes with a Cell Removal Solution ("CRsol") and an Epidermis Removal Solution ("ERsol"). Multiple scenarios were tested, including the order and number of washes. Various options produce more or less acceptable results. However, preferably, there is a wash in CRsol first, a wash in ERsol next, normally the epidermis is then removed, followed by another CRsol wash. It is possible to introduce additional washes and changes of the wash solutions to fresh solutions. However, if the ERsol wash occurs first, the epidermis removal is difficult and inefficient. All the washes are preferably performed at room temperature and the volume of skin to solution is at least 1:1 or more, with 1:3 being preferred.

The preferred CRsol and ERsol include detergents (two or more detergents in the CRsol, preferably deoxycholate (3,12 a-dihydroxy-5(3-cholan-24-oic acid) and either Triton® X-100, octoxynol or polysorbate). Preferably, no enzymes are added to either the ERsol or CRsol. Enzymes might compromise the matrix and, if enzymes are present, the cells and epidermis removal is typically not optimal. The ERsol contains at least about 0.5M NaCL or an equivalent salt.

The washes in CRsol are for 1-48 hours, each. The CRsol composition can be the same (but does not have to be identical) for the two washes using CRsol. The wash in ERsol is for 1 to 72 hrs, or longer. The Extra-Thick or full-thickness skin products will usually require a longer ERsol wash and CRsol wash, each for up to about 72 hrs. It will also involve at least one change of the ERsol, after an overnight wash of about 1-24 hours.

The preferred CRsol is a phosphate buffered saline solution containing Ethylenediaminetetraacetic Acid (EDTA) or another chelating agent and large concentrations of detergent(s). A preferred detergent is deoxycholate. More preferably, the solution contains about 1.0 to 10% deoxycholate and yet more preferably, about 5% deoxycholate. In an alternative preferred embodiment, the CRsol contains two detergents and, preferably, one of the two detergents is deoxycholate at the above-indicated concentrations. The second detergent may be, for example, polyethylene glycol p-tert-octylphenyl ether (Triton® X-100), sodium dodecyl sulfate or polysorbate. A preferred second detergent is Triton® X-100 at about 0.5-5.0%, preferably at about 0.75%. The chelating agent is preferably EDTA at a concentration of 0.005 to 0.05 M, preferably 0.01 M. The solutions are typically made up to a pH of about 7.0-10.0, preferably about 8.5. Phosphate buffer solutions are well known, can easily be prepared and are available also commercially.

By contrast, the ERsol is a water-based solution containing electrolytes, EDTA or another chelating agent and limited concentrations of detergent(s). For example, for full thickness skin processing, in a preferred embodiment, the ERsol might comprise, Triton® X-100 detergent at a concentration of less than about 0.2%, preferably at about 0.05%, and an electrolyte such as sodium chloride at a concentration of 0.5 to 2.0 M, preferably about 1.2 M. The chelating agent is preferably EDTA at a concentration of 0.05 to 0.5 M, preferably about 0.1 M. The solutions are typically made up to a pH of about 6.5-10.0, preferably about 8.0.

However, for extra thick skin, the ERsol might include somewhat larger amounts of detergent(s) than the ERsol for full thickness skin processing and might comprise also a pH buffer. For example, in a preferred embodiment, the ERsol might comprise Triton® X-100 at a concentration of less than about 2.0%, preferably at a concentration of less than about 1%, and more preferably at about 0.7%, and deoxycholate at a concentration of 1.0-4.0%, preferably about 2%. The electrolyte is preferably sodium chloride at a concentration of 0.5 to 2.0 M, preferably about 1.0 M. The chelating agent is preferably EDTA at a concentration of 0.05 to 1.0 M, preferably 0.15 M. The pH buffer is preferably phosphate at a concentration of about 0.05-0.5, typically about 0.15 M. The solutions are typically made up to a pH of about 6.5-10.0, preferably about 8.0.

At the end of this process, the skin is practically free of any cellular content. After the ERsol treatment, the epidermis is removed easily by dissecting apart the two layers. In a preferred, optional embodiment, the last wash, after the epidermis removal, is another at least one CRsol wash.

The skin is next exposed to a wash in a Gamma Irradiation Protection Solution ("GIPS"). The GIPS contains at least two sugars. One preferred sugar is trehalose. Other preferred sugars might be maltose, dextrose or fructose. The preferred GIPS is about 10% to 50% of trehalose and one or more other sugars, such as 10% to 50% maltodextrin, in phosphate saline buffer. The wash in the GIPS is at room temperature for 0.5 to 24 hrs, in at least 1:1 to 1:5 (v:v) (skin:solution), with agitation at a speed of at least 50 rpm to 200 rpm.

After the GIPS wash, the skin is placed on a cutting board, inspected and is cut into pieces of the desired size and shape. The produced allograft pieces might be small, about 1×1 cm for certain procedures, e.g. gingivitis treatment (cover the root of teeth), or larger, e.g. about 20×20 cm for larger burns or wounds. A variety of instruments may be used to cut the dermis, including a scalpel or a laser-cutting instrument. Of course, the surgeon will likely further shape and trim the graft as needed, before implantation.

The allograft pieces are next placed onto a meshed material. Use of mashed backing material is known in the art. The material is typically bio-compatible. It is placed in a manner to identify the basal membrane side of the allograft. The mashed material improves the ease of handling of the allograft, the ease of use of the allograft by the surgeon, and identifies the side of the allograft where the basement membrane layer is located. The dermis is then placed into a container. The container may be of a suitable material including glass, plastic, or, preferably, Poly-Tyvek® or similar pouches, having at least one porous side. Multiple allograft pieces from the same donor may be stored in one container/pouch. In a preferred embodiment, each allograft piece is stored in a separate pouch. The pouches may be stored at a temperature from about 1° C. to about 100 C prior to the next step. Typically, a measurement of the resulting tissue thickness is undertaken.

Alternative approaches are available next, prior to the irradiation step. At least one of these various alternative approaches is taken. In accordance to one alternative embodiment, the tissue is frozen to at least about −20° C. or colder, preferably −40° C. or colder, up to about −80° C.

In accordance to another alternative embodiment, the tissue, is placed in a container in a normal saline media and kept at room (ambient) temperature before the sterilization/irradiation step. Of note, for tissue that is stored in saline, the previous step of a wash in GIPS solution is optional.

In accordance to a preferred alternative embodiment, the tissue, prior to sterilization is subject to a lyophilization step, to remove water content from the allograft. The lyophilization process is time and temperature sensitive. The lyophilization is carried out by standard procedures known in the art. See, for example, D. Michael Strong and Allen P. MacKenzie, Freeze-drying of Tissues (Chapter 5 and references included therein) in Musculoskeletal Tissue Banking, edited by William W. Tomford, Raven Press (1993). The lyophilization approach includes a step of testing a few sacrificed samples for their moisture content as a quality check for the lyophilization process. AATB requirements are that the residual moisture is between 0 and 6%.

Optionally, the dermal allograft pieces, if lyophilized, may be stored at 1° C. to 10° C. after processing and before sterilization, for up to about 1 year. If frozen, the tissue could be stored at about −40° C. or colder preferred for up to at least one year before sterilization.

The allograft pieces in a container (e.g. the Poly-Tyvek® bags, glass bottles, etc.) are transferred to special designed containers for sterilization.

In a preferred embodiment, the sterilization is accomplished by irradiation. It is desired that the irradiation have a short wavelength to enhance penetration of the radiation into and throughout the dermal tissue. Preferably, the radiation used to achieve sterilization of the dermis is γ-radiation. The sterilization is enhanced because the γ-radiation can provide complete penetration of the container, packaging and dermal tissue and provide a more predictable bacterial, viral, or fungal inactivation. Microorganisms, including both enveloped and non-enveloped RNA and DNA viruses, are susceptible to inactivation by γ-radiation. Additionally, any remaining cells, if any, will be inactivated by the irradiation.

The inventor tested many irradiation sources, energies and protocols. In a preferred embodiment, the sterilization is by Cesium$^{137}$ or Cobalt$^{60}$ γ-radiation. In a yet more preferred embodiment, the sterilization is by Cobalt$^{60}$ radiation. It will be recognized by an artisan skilled in the art that Cobalt$^{60}$ produces a particularly short wave-length energy within the gamma ray range, and the short wave energy is highly penetrative.

The irradiation is carried out in a temperature-controlled environment, at between −30° C. (typically, in dry ice) to room ambient temperature, although it is preferred to irradiate at below 10° C. The preferred temperature at which irradiation is performed is dependent on the state of the sample. A sample which is frozen is irradiated while maintaining the temperature such that the sample remains frozen. A sample which has been previously lyophilized or stored in saline is irradiated preferably at a cool temperature, preferably below 10° C. and more preferably at about 0-4° C.

The processed dermal allograft pieces are placed in containers or vials suitable for the irradiation. These containers/vials can be constructed of various materials, including plastic and glass. The process is optimized and monitored for reproducible dose delivery of the radiation. In a preferred embodiment, the sterilization occurs in a temperature-controlled environment at from about −20° C. to room temperature. The effective dose of absorbed irradiation is from about 5-35 kiloGrays ("kGy"). Preferably, the absorbed dosage is from 10-30 kGy, and more preferably from 10-23 kGy. It will be recognized by an artisan skilled in the art that 5-35 kGy are very high levels of absorbed radiation.

The resultant allograft dermal tissue is now virtually acellular, pliable, and has a somewhat reduced basement membrane volume. The irradiated allograft has a bioburden load reduced by at least a factor of $10^{-4}$ (4 logs). Typically, the bioburden is reduced to at least about the Sterility Assurance Level (SAL) of $10^{-6}$.

It is also understood that the irradiation techniques, procedures, and methodologies employed by the current invention comply with standards and requirements known to those skilled in the art. The effectiveness and efficiency of the irradiation of the grafts depends on several factors, such as the duration of time during which a dosage of irradiation is applied, the type of irradiation, the distance the source of the irradiation is from the sample, any shielding effects, and other considerations as can be contemplated by those of ordinary skill in the art. For example, that the radiation may have to penetrate various other surfaces and materials, such as through a box containing samples of dermal allografts within vials that may contain a fluid or other packaging materials/systems. The factors that should be accountable include, for example, the size and volume of vials, and their density and configuration. In all cases, the radiation must uniformly, effectively and efficiently penetrate the cardboard of the box and the allograft container material (e.g. a bag, or a vial, etc., typically a vial, made of, for example, glass or plastic) and be able to deliver effectively the targeted absorbed dose uniformly in a tight range to the dermal allografts to provide the degree of bioburden reduction of the current invention.

The irradiation process is often outsourced to firms with sophisticated irradiation machinery, such as Nordion™ Inc., Ottawa, Ontario, Canada or STERIS™ Corporation, Mentor, Ohio. Various methods known in the art are employed to determine the quality of the product, its microbial load, transparency, and pliability. Such quality monitoring steps may involve the sacrifice of some processed grafts for specific testing purposes.

In a preferred embodiment, the irradiation is delivered for a duration of from about 30 to about 300 minutes. The duration of the irradiation dosage can be a factor of the half-life of the -y-irradiation source. Of course, the duration of the dosage may be influenced by the various factors described above or other factors known to those knowledgeable in the art.

Given these variables, to consistently achieve the desired exposure levels within the range of (5-35 KGy) one must methodically standardize, control and monitor all aspects of the irradiation process. The irradiation dose needed for sterilization is validated on a regular basis, typically at least once per calendar quarter by a recognized scheme for sterility such as VD max 15—described in ANSI/AAMI/ISO 11137-1:2006: Sterilization of Health Care Products. Additionally, exposure is monitored in each run by dosage mapping to insure proper dosing.

During transport of the sterilized allograft, the container and/or storage device housing the media solution, if used, and the allograft, once irradiated, are preferably not exposed to the environment, which could lead to a loss of sterility. Thus, once irradiated, the allograft preferably will not be exposed to further processing or changing of media. However, sterilization may take place earlier in the chain of events, followed by aseptic handling of the tissue.

After sterilization, the dermal graft material is preferably stored at a temperature from 1° C. to 10° C. and it may be stored at ambient temperature. Of course, if the frozen option was selected before sterilization, the allograft must remain in a frozen state until it is prepared for surgical use. However, there is no detrimental effect on the allograft if storage is at any temperature, from about −80° C. to about 30° C.—again with the exception of the frozen option.

Shelf life is a function of packaging and the intrinsic stability of the content, itself. A sterilized graft in a robust, closed container described herein remains sterile and useful for at least up to about 3 years, or longer. Testing of tissue pliability, cell content, medical records review, process quality steps as well as bioburden testing are performed prior to and after sterilization procedures of the dermal allografts in the current invention.

The reduction in allergenic cells and microorganisms levels in the processed tissue provides a safer allograft, much less likely to trigger an immune reaction from the patient and less likely to produce infections. Microbial contaminations are virtually eliminated based on the incoming bioburden and the sterilization to a SAL of $10^{-6}$. The sterilized acellular dermal allograft was tested and shown to compare well with other dermal grafts in respect to physical characteristics, such as pliability, the ability to undergo cell repopulation, and effectiveness in repairing wounds or other soft tissue repairs. The inventor performed animal testing and concluded that the immune response to the allograft is limited and not a clinically important factor in the utility of the tissue.

Several animal studies compared non-irradiated acellular dermal graft and γ-irradiated acellular dermal graft. The studies included short and long term studies in different animal models. In one animal study, human ACD was transplanted to rat. The recellularization and revascularization between irradiated and non-irradiated human ACD were compared in this model. A three-month study was performed to compare longer-term reactions and regeneration between irradiated and non-irradiated ACD in a rat to rat experiment. In a third animal study, human ACD was implanted in rabbit (an abdominal wall repair model) to compare adhesion rate, recellularization and revascularization between irradiated and non-irradiated ACD. These animal model studies showed equivalent repair between the irradiated dermis and non-irradiated dermis, as demonstrated by comparing re-cellularization, revascularization and adhesion. The irradiated allograft showed the same limited adhesion property on the basement membrane surface as the non-irradiated allograft. The irradiated allografts compared well with the results obtained with non-irradiated dermis.

The current invention provides a sterile dermal allograft. The dermal allograft may be used in any soft tissue repair and reconstruction, such as but not limited to breast reconstructive surgery; abdominal wall repair; orthopedic surgery;

dental surgery; plastic and reconstructive surgery; dental procedures; burn surgery; etc. The allograft is a dermal allograft sterilized by ionizing radiation in a controlled temperature environment of from about −20° C. to 50° C. with an effective dose of absorbed irradiation from about 10-30 kGy, to achieve a preferred SAL of $10^{-6}$. The allografts of the current invention have reduced enzymatic and metabolic activity, and reduced antigenic properties. The irradiated dermal allograft of the invention is pliable and is capable of effective re-population by the patient's own cells, in situ or, for that matter, in-vitro. The matrix is not only sterile and cell free, it is architecturally intact. The sterilized matrix can be used as a scaffold for cell culturing procedures/techniques.

The properties of the allograft of the invention have been demonstrated repeatedly by histopathology and electron microscopy studies. The terminally sterilized acellular dermal allograft has a reduced count of viable human cells. In testing of the processed allograft, there have been no viable cells observed, resulting in the dermal graft having reduced immunogenicity. Additionally, the sterilized graft has an essentially intact collagen structure. The intact collagen structure plays a large role in the tissue's ability to maintain its effectiveness for grafting procedures. Albeit the basal membrane content is not a particular concern of the procedure, it has been noted that the basal membrane is present, albeit slightly reduced in volume.

The irradiation process causes a limited amount of cross-linking of the structural elements of the graft, resulting in a slightly more sturdy structure. The allograft requirements differ, based on surgical application and surgeon's preferences. The invention allows also for the modification of the toughness/ductility (ability to stretch) of the tissue by irradiation, within the irradiation ranges specified for the invention. As an example, the inventor has tested ductility over the preferred dose range of 10-23 kGy. The ductility of dermis dropped about 11.6% over this range, which was statistically significant. Using the entire range of 10-30 KGy would give the ability to further control ductility. In another example, the dermal graft ductility was conducted using a standard uniaxial tension test. Fifty-two dermal graft tensile bars were tested. The series constituted three donors (with three matched sets) of non-irradiated and γ-irradiated tensile testing specimens. The absorbed radiation was at 17 to 23 kGy for freeze-dried derma, in each test. The non-irradiated samples failed with strain at maximum load of 58.6%, the irradiated tissue failed with strain at 47%. This decrease in ductility was barely significant at a 95% confidence level (p-value<0.05).

The allograft is typically stored at a temperature from 1° C. to 10° C. Moreover, there is no detrimental effect on the allograft if storage is at any temperature, from about −80° C. (colder if different packaging is used) to about 30° C. (Exception to this range is the frozen option, previously noted above). The long storage of the terminally sterilized acellular dermal graft is a significant advantage whereby the graft can be stored for various periods and maintain its effectiveness for use. For example, the graft of the current invention can be stored after sterilization for up to about 3 years or more, while maintaining the sterility, pliability, ductility and reduced immunogenicity.

It is understood that the specific order or hierarchy of steps in the methods disclosed herein are but exemplary approaches. The specific order or hierarchy of steps in the method can be rearranged while remaining within the scope and spirit of the present invention. For example, but not limited to this example, the processing may occur at the same facility where tissue is recovered; bio burden checks can be initially taken at time of tissue recovery and/or upon arrival at the processing center; or irradiation may take place before removal of the epidermis or at other time points, for example after the processing and thus being a "terminal" step in the method of preparation.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method of preparing an irradiation sterilized acellular dermal allograft that can be stored for periods of at least about 3 years before use in grafting procedures, the method comprising:
  processing skin tissue comprising the following steps in the order of:
  (i) removing the cells of the skin tissue by exposing said skin tissue to a cell removal solution to remove cells and provide a first processed skin tissue, said cell removal solution comprising at least two detergents: (1) deoxycholate at a concentration about 1% to 10% (v:v); and (2) a polyethylene glycol p-tert-octylphenyl ether, sodium dodecyl sulfate, or polysorbate at a concentration about 0.5% to 5% (v:v);
  (ii) deteriorating the epidermis by exposing the first processed skin tissue to a separate epidermis removal solution comprising at least one detergent at a concentration about 0.2 to 2.8% (v:v) to deteriorate the epidermis of the first processed skin tissue and form a second processed skin tissue;
  wherein the cell removal and epidermis removal solutions do not contain enzymes;
  (iii) removing the epidermis of the second processed skin tissue after exposure to the epidermis removal solution to produce a dermal allograft;
  (iv) exposing the dermal allograft to a gamma irradiation protection solution;
  (v) preparing the dermal allograft for irradiation by performing at least one step from among: drying the dermal allograft by lyophilization, freezing the dermal allograft, or placing the dermal allograft in saline; and
  (vi) exposing the prepared dermal allograft to irradiation;
  whereby the skin tissue can then be stored until use for periods of up to at least about 3 years.

2. The method of claim 1, wherein the gamma irradiation protection solution comprises at least two sugars and one sugar is trehalose.

3. The method of claim 1, which further comprises placing the dermal allograft in a container after exposing the dermal allograft to the gamma irradiation protection solution, wherein the container is a bag made of polyethylene and/or polyester laminated with spunbond high density polyethylene fibers.

4. The method of claim 1, wherein the skin tissue is placed in a stabilization media prior to exposure to processing with the cell removal solution.

5. The method of claim 4, wherein the stabilization media is a cell growth media which contains an antibiotic.

6. The method of claim 1, wherein the step of preparing the allograft for the irradiation step is by lyophilization of the allograft.

7. The method of claim 1, wherein the step of preparing the allograft for the irradiation step is by freezing of the allograft.

8. The method of claim 1, wherein the step of preparing the allograft for irradiation comprises placing the allograft in saline inside a container.

9. The method of claim 1, wherein after the step of preparing the allograft for irradiation, the allograft may be stored for up to about one year before irradiation.

10. The method of claim 1, wherein the irradiation is gamma irradiation.

11. The method of claim 1, wherein the irradiation is from $Cobalt^{60}$ or $Cesium^{137}$.

12. The method of claim 11, wherein the irradiation is from $Cobalt^{60}$.

13. The method of claim 11, wherein the irradiation delivers an absorbed radiation dose of 5-35 kGy.

14. The method of claim 13, wherein the absorbed radiation dose is about 10-23 kGy.

15. The method of claim 13, wherein the absorbed radiation dose is about 17-23 kGy.

16. The method of claim 1, comprising a further step, before the processing step, storage of the skin tissue in glycerol at −20° C. to 10° C. for up to about 5 years.

17. The method of claim 16, wherein prior to storage in glycerol, the graft is treated by exposure to at least two increasing concentration of glycerol, the lowest concentration being about 25% (v:v) and the highest about 100% (v:v).

18. The method of claim 17, wherein the exposure to increasing concentration of glycerol, comprises exposure to 50%, 75% and 100% glycerol (v:v).

19. The method of claim 1, wherein the cell removal solution of step (i) further comprises a phosphate buffered saline solution containing a chelating agent.

20. The method of claim 1, wherein the epidermis removal solution of step (ii) further comprises a water-based solution that includes electrolytes and a chelating agent.

21. The method of claim 1, wherein the two detergents in the cell removal solution are at a combined concentration of at least 5.5%.

* * * * *